United States Patent [19]

Dreikorn et al.

[11] 4,381,312

[45] Apr. 26, 1983

[54] 2,4,6-TRINITRODIPHENYLAMINES FOR CONTROL OF FOLIAR PHYTOPATHOGENS

[75] Inventors: Barry A. Dreikorn; Kenneth E. Kramer, both of Indianapolis, Ind.

[73] Assignee: Eli Lilly and Company, Indianapolis, Ind.

[21] Appl. No.: 532,436

[22] Filed: Dec. 13, 1974

[51] Int. Cl.[3] .................... A01N 33/02; A01N 37/10; A01N 37/34
[52] U.S. Cl. .................................. 424/304; 424/309; 424/330
[58] Field of Search .................. 424/304, 330, 309

[56] References Cited

U.S. PATENT DOCUMENTS 4,041,172  8/1977  Barlow ................................ 424/304

FOREIGN PATENT DOCUMENTS 2363602  6/1974  Fed. Rep. of Germany .
721370  1/1972  So. Africa .

Primary Examiner—Allen J. Robinson
Attorney, Agent, or Firm—Kathleen R. S. Page; Joseph A. Jones; Leroy Whitaker

[57] ABSTRACT

A class of 2,4,6-trinitrodiphenylamines, bearing one or more substituents on the ring which does not bear nitro groups, which substituents are chosen from among trfluoromethyl groups, nitro groups, and other simple substituents, are effective in the control of foliar phytopathogens.

9 Claims, No Drawings

2,4,6-TRINITRODIPHENYLAMINES FOR CONTROL OF FOLIAR PHYTOPATHOGENS

BACKGROUND OF THE INVENTION

This invention belongs to the field of agricultural chemistry and relates to the protection of plants from disease.

Agricultural chemical research has produced a great number of plant protective agents, and research continues to produce new ones every year. A number of publications have disclosed plant-protective compounds which constitute the background of this invention.

For example, British Pat. No. 845,916 discloses that a family of N,N-dialkylanilines, which can bear three nitro groups, are useful as plant fungicides.

Roberts, Ind. Eng. Chem. 34, 497-498 (1942), and Goldsworthy et al., J. Ag. Research 64, 667-678 (1942) discussed phytopathological testing of diphenylamine compounds including 2,4-diaminodiphenylamine and 4-nitrodiphenylamine.

Belgian Pat. No. 780,549 discloses halo-substituted diphenylamines which can bear nitro groups. However, the Belgian patent describes compounds containing at least four halogen atoms, and the phenyl rings of the compounds are alternatively substituted with a variety of groups such as carboxy, sulfonamido, perhalocarbyl, hydrocarbylamino and so forth.

German Offenlegungsschrift No. 2,363,602, published June 27, 1974, describes a group of diphenylamines having diverse substituents, some of which are the same as the substituents of the compounds of this invention.

SUMMARY OF THE INVENTION

The present invention is a method of reducing the adverse effects of foliar phytopathogens which comprises contacting the phytopathogens on the foliage of plants with an effective amount of a compound of the formula

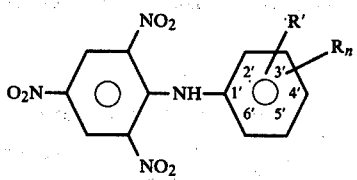

wherein R represents
nitro,
trifluoromethyl,
hydroxy,
cyano,
benzoyl, or
$C_1$-$C_3$ alkoxycarbonyl;
n represents 1-3;
R' represents
hydrogen,
chloro, or
$C_1$-$C_3$ alkyl;
provided that benzoyl and $C_1$-$C_3$ alkoxycarbonyl do not occupy either the 2'- or 6'-position; that nitro does not occupy either the 2'- or 6'-position when n represents 1; that n must represent 1 when R represents cyano, benzoyl or $C_1$-$C_3$ alkoxycarbonyl; and that R' represents hydrogen when n represents 3.

The compounds are especially useful for the control of foliar phytopathogens of grapes.

DESCRIPTION OF THE PREFERRED EMBODIMENT

In the above formula, the chemical terms are used in their normal meanings. For example, the term $C_1$-$C_3$ alkyl refers to groups such as methyl, ethyl and isopropyl. The term $C_1$-$C_3$ alkoxycarbonyl refers to groups such as methoxycarbonyl, ethoxycarbonyl and isopropoxycarbonyl.

All the compounds named herein are named as trinitrodiphenylamines in the interest of uniformity, even though the rules of nomenclature may call for some compounds to be named otherwise.

The compounds below are typical of the compounds used in the invention. It will be understood that the named compounds do not delineate the scope of the invention, but are named merely to help those of chemical skill to understand the invention.

2',4'-bis(trifluoromethyl)-2,4,6-trinitrodiphenylamine
3',4',5'-trifluoro-2,4,6-trinitrodiphenylamine
2',4',6'-trihydroxy-2,4,6-trinitrodiphenylamine
3'-chloro-2,4,5',6-tetranitrodiphenylamine
4'-ethyl-2,2',4,6,6'-pentanitrodiphenylamine
4'-chloro-2'-trifluoromethyl-2,4,6-trinitrodiphenylamine
4'-chloro-3',5'-bis(trifluoromethyl)-2,4,6-trinitrodiphenylamine
2'-hydroxy-4'-isopropyl-2,4,6-trinitrodiphenylamine
3'-cyano-5'-methyl-2,4,6-trinitrodiphenylamine
3'-benzoyl-2'-methyl-2,4,6-trinitrodiphenylamine
2'-ethyl-5'-methoxycarbonyl-2,4,6-trinitrodiphenylamine
3'-chloro-2',5'-dihydroxy-2,4,6-trinitrodiphenylamine
4'-chloro-3'-cyano-2,4,6-trinitrodiphenylamine
2'-methyl-4'-trifluoromethyl-2,4,6-trinitrodiphenylamine
3'-chloro-5'-ethoxycarbonyl-2,4,6-trinitrodiphenylamine
4'-benzoyl-2'-chloro-2,4,6-trinitrodiphenylamine
3'-methyl-4'-propoxycarbonyl-2,4,6-trinitrodiphenylamine The compounds used in the practice of this invention are easily synthesized by the reaction of picryl chloride with an appropriately substituted aniline. The reaction is readily accomplished in an alkanol at room temperature. An acid scavenger, such as an inorganic base, triethylamine or excess of the aniline intermediate, is needed. When a 2',6'-disubstituted compound is to be made, the reaction goes more effectively in the presence of NaH in a solvent such as dimethylformamide at reduced temperature. The reactions are carried out in anhydrous media and it is best to blanket the reaction vessel with inert gas.

The intermediates, picryl chloride and substituted anilines, are of course readily obtained. The following preparative example illustrates a typical synthesis.

EXAMPLE 1

4'-trifluoromethyl-2,4,6-trinitrodiphenylamine

A 5 g. portion of picryl chloride and 3.25 g. of 4-amino-α,α,α-benzotrifluoride were dissolved with 10 ml. of triethylamine in 100 ml. of ethanol. The reaction mixture was stirred at room temperature overnight. It was then filtered, and the precipitate was recrystallized from ethanol to yield 5.13 g. of 4'-trifluoromethyl-2,4,6- trinitrodiphenylamine, m.p. 171°–172° C. The compound was identified by nuclear magnetic resonance analysis and elemental microanalysis, the results of which follow.

|   | Theoretical | Found |
|---|---|---|
| C | 41.95% | 42.23% |
| H | 1.90 | 2.13 |
| N | 15.05 | 14.84 |
| F | 15.31 | 15.36 |

The above exemplary synthesis is typical of the preparations of all of the compounds of the invention, such as the following.

EXAMPLE 2

3'-ethoxycarbonyl-2,4,6-trinitrodiphenylamine, m.p. 149°–150° C.

EXAMPLE 3

2,2',4,4',6,6'-hexanitrodiphenylamine

EXAMPLE 4

2,3',4,6-tetranitrodiphenylamine, m.p. 210°–211.5° C.

EXAMPLE 5

2,4,4',6-tetranitrodiphenylamine, m.p. 218°–221° C.

EXAMPLE 6

2'-hydroxy-2,4,6-trinitrodiphenylamine, m.p. 200°–201° C.

EXAMPLE 7

3'-trifluoromethyl-2,4,6-trinitrodiphenylamine, m.p. 151°–152° C.

EXAMPLE 8

4'-cyano-2,4,6-trinitrodiphenylamine, m.p. 185°–187° C.

EXAMPLE 9

4'-hydroxy-2,4,6-trinitrodiphenylamine, m.p. 169°–170° C.

EXAMPLE 10

2'-trifluoromethyl-2,4,6-trinitrodiphenylamine, m.p. 211°–212° C.

EXAMPLE 11

2'-chloro-5'-trifluoromethyl-2,4,6-trinitrodiphenylamine

EXAMPLE 12

2'-methyl-2,4,5',6-tetranitrodiphenylamine, m.p. 218°–223° C.

EXAMPLE 13

4'-benzoyl-2,4,6-trinitrodiphenylamine, m.p. 198°–199.5° C.

EXAMPLE 14

3'-hydroxy-2,4,6-trinitrodiphenylamine, m.p. 210°–211° C.

EXAMPLE 15

3',5'-bis(trifluoromethyl)-2,4,6-trinitrodiphenylamine, m.p. 180°–181° C.

EXAMPLE 16

3'-cyano-2,4,6-trinitrodiphenylamine, m.p. 180.5°–181° C.

EXAMPLE 17

2'-cyano-2,4,6-trinitrodiphenylamine, m.p. 213°–215° C.

EXAMPLE 18

4'-ethoxycarbonyl-2,4,6-trinitrodiphenylamine, m.p. 181°–183° C.

The compounds described above have been shown, in a number of in vivo tests, to protect plants from the adverse effects of foliar phytopathogens. The following examples illustrate the tests employed and the results produced by representative compounds.

Each compound was formulated for testing by dissolving or suspending about 3.5 weight percent of it in 50:50 acetone:ethanol containing about 10 g./100 ml. of a nonionic surfactant. Pure ethanol was used as the solvent in some downy mildew tests. The solution was then dispersed in deionized water in a quantity such that the water dispersion contained the various compound concentrations used in the various tests described below. The concentrations are measured in parts per million by weight.

The compound dispersions were applied to the test plants by spraying them with an atomizer using sufficient dispersion to wet the plants thoroughly.

Untreated, infected controls and untreated, normal controls were included in each test. The results are reported on a 1–5 rating scale where 1 indicates severe disease and 5 indicates complete control of the disease. A dash in the tables below indicates that the compound was not tested at the rate indicated. In some cases, more than one test was performed against a given phytopathogen, and the results in such cases are reported as averages. Compounds are identified by their example numbers.

Test 1 downy mildew of grape

Young expanding grape leaves were detached from healthy vines on the day of the test. Leaves were placed individually in plastic petri dishes, bottom side up, on top of an expanded plastic mat. Water was added to each petri dish, and the petiole of each leaf was wrapped with a water-soaked wad of cotton. Each leaf was sprayed with an aqueous dispersion of the compound to be tested.

After the test compound dispersions had dried, the leaves were inoculated by atomizing a conidial suspension of *Plasmopara viticola* (grown on infected leaf tissue) evenly over the leaf surface. The plates were then covered and were stored in a growth room at about 18° C. and 100% relative humidity where they were exposed to eight hours a day of artificial light. After about a week of storage, when the infected controls were heavily infected with downy mildew, all the leaves were observed and the symptoms of disease were recorded.

| Example | Disease Rating Compound Concentration, ppm. | | | | |
|---|---|---|---|---|---|
| No. | 800 | 400 | 100 | 50 | 25 |
| 1 | 5 | 5 | 5 | 5 | 3 |
| 2 | 3 | 1 | — | — | — |
| 3 | — | 5 | 5 | — | — |
| 4 | — | 5 | 5 | — | — |
| 5 | — | 5 | 5 | — | — |
| 6 | 3 | 2 | 1 | — | — |
| 7 | 5 | 5 | 4 | 4 | 3 |
| 8 | 5 | 5 | 5 | 4 | 3 |
| 9 | 3 | 3 | — | — | — |
| 10 | 2 | 1 | — | — | — |
| 11 | 5 | 5 | — | — | — |
| 12 | 5 | 5 | — | — | — |
| 13 | 3 | 1 | — | — | — |
| 14 | 5 | 5 | 3 | 3 | 1 |
| 15 | 5 | 5 | 5 | 5 | 5 |
| 16 | 3 | 4 | — | — | — |
| 17 | 4 | 3 | — | — | — |
| 18 | 4 | 2 | — | — | — |

Tests were also conducted against downy mildew of grape vines growing in field plots. A preferred compound, 4'-trifluoromethyl-2,4,6-trinitrodiphenylamine was found to provide 95–97 percent control of downy mildew. The compound was formulated as an emulsifiable concentrate containing 120 g./liter, and was applied to the foliage on a 7–10 day schedule at 600 ppm. concentration. The disease was extremely severe, affecting about 80 percent of the foliage in untreated control plots. No leaf or fruit injury was caused by the compound.

Test 2 apple scab of apple

Apple seedlings at the 4–6 leaf stage were sprayed with aqueous dipsersions of the test compounds. The following day, the plants were sprayed with a suspension of fresh conidia of *Venturia inaequalis* obtained from infected apple seedlings kept as a source of inoculum. The plants were held for two days in a 20° C. moist chamber to start disease growth and were then transferred to the greenhouse. About two weeks after application of the compounds, the plants were observed and the results were recorded.

| Example | Disease Rating Compound Concentration, ppm. | | | |
|---|---|---|---|---|
| No. | 1200 | 800 | 400 | 200 |
| 1 | 5 | 3 | 3 | 1 |
| 7 | 5 | 1 | 1 | — |
| 8 | 1 | 1 | 1 | — |
| 14 | — | 5 | 1 | 1 |
| 15 | — | 5 | 5 | 5 |

Test 3 cercospora leaf spot of sugar beet

Sugar beet seedlings were transplanted into square plastic pots, allowed to grow for three weeks, and aqueous dispersions containing the compounds to be tested were sprayed on the leaf surfaces. After the dispersions dried, but within 24 hours, the plants were inoculated with a conidial suspension of *Cercospora beticola* which had been grown on sugar beet leaf decoction agar. After the plants were held in a moist chamber for two days, they were transferred to the greenhouse and observed 2–3 weeks later.

| Example | Disease Rating Compound Concentration, ppm. | | |
|---|---|---|---|
| No. | 800 | 400 | 200 |
| 1 | 4 | 4 | 1 |
| 7 | 4.5 | 2.5 | 3 |
| 8 | 1 | 1 | 1 |
| 14 | 1 | 1 | 1 |
| 15 | 4 | 4 | 4 |

A preferred compound, 4'-trifluoromethyl-2,4,6-trinitrodiphenylamine, was tested against an infection of *C. beticola* on sugar beets growing in the field. Dispersions of the compound were applied three times on a 14-day spray schedule. The compound was formulated as an emulsifiable concentrate containing about 120 g. of compound per liter of concentrate. When the disease control was rated, two weeks after the last treatment, it was found that 74 percent control was obtained from application of 600 ppm. dispersions, and 87 percent control from 1200 ppm. dispersions.

Test 4 botrytis of grape

Sound grape berries were sterilized by immersion in diluted sodium hypochlorite and thoroughly rinsed. The berries were placed on wire screen shelves in compartmented Pyrex plates. The berries were then flamed and sprayed with test chemical dispersions. The following day, the berries were inoculated by spraying 5 ml. of a conidial suspension of *Botrytis cinerea* over each plate containing 12 berries. The inoculum had been grown on frozen lima bean agar. A small amount of water was added to each plate and a cover was sealed over each plate. After 48 hours at 25° C., the berries were observed and disease ratings recorded.

| Example | Disease Rating Compound Concentration, ppm. | | | |
|---|---|---|---|---|
| No. | 800 | 400 | 200 | 100 |
| 1 | 2.5 | 2.5 | 1 | — |
| 2 | 1 | 1 | 1 | — |
| 3 | — | 2 | 1 | 1 |
| 4 | — | 1 | 1 | 1 |
| 5 | — | 2 | 2 | 1 |
| 6 | 1 | 1 | 1 | — |
| 7 | 2 | 2 | 1 | — |
| 8 | 1 | 2 | 1 | — |
| 9 | 1 | 1 | 1 | — |
| 10 | 1 | 1 | 1 | — |
| 11 | 2 | 3 | 2 | — |
| 12 | 1 | 1 | 2 | — |
| 13 | 1 | 1 | 1 | — |
| 14 | 1 | 1 | 1 | — |
| 15 | 3 | 1 | 1 | — |
| 16 | 1 | 1 | 1 | — |
| 17 | 1 | 1 | 1 | — |
| 18 | 1 | 1 | 1 | — |

The compound of Example 1 was tested against an infection of *B. cinerea* on faba bean (horsebean) growing in field plots. The compound, formulated as an emulsifiable concentrate containing about 120 g./liter, was applied six times on a 7–10 day spray schedule. When the disease control was rated, about two weeks after the last application, an extremely severe infection was found on the control plots. The compound, applied at 600 ppm.

concentration, gave 40 percent control of the disease, and gave 55 percent control at 1200 ppm. concentration.

Test 5
broad spectrum test

Typical compounds were evaluated in a broad spectrum test containing five representative foliar phytopathogens. The individual tests were performed as follows.

late blight of tomato

Four-week-old tomato seedlings were sprayed with aqueous dispersions containing 400 ppm. of the test compounds. The following day, the foliage was inoculated with an aqueous suspension of propagules of *Phytophthora infestans*. The inoculum had been reared on infected wheat seed. The plants were held for two days in a moist chamber to start disease growth, and were then transferred to a greenhouse. The plants were observed and rated for disease control about one week after application of the test compounds.

powdery mildew of bean

The host plants were 10-day-old bean seedlings. After aqueous dispersions containing 400 ppm. of the test compounds had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

anthracnose of cucumber

Aqueous dispersions containing 400 ppm. of the test compounds were applied to healthy cucumber seedlings grown in sterilized greenhouse soil. The following day, the plants were inoculated with *Colletotrichum lagenarium* conidia as an aqueous suspension. The fungus had been grown on potato dextrose agar in petri dishes. The plants were held in a moist chamber for two days and transferred to the greenhouse. The disease was observed and rated approximately 12 days after application of the test compounds.

rice blast of rice

The test compound dispersions, containing 400 ppm. of the compounds, were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5-7 days and observed.

helminthosporium leaf spot of wheat

Healthy wheat seed was planted in sterile greenhouse soil. When the seedlings were 4-5 inches tall, they were sprayed with 400-ppm. test compound dispersions. The day after treatment, the plants were inoculated with a spore suspension of *Helminthosporium sativum* which had been grown on potato dextrose agar. The plants were placed in a moist growth chamber for two days, and then transferred to the greenhouse. About a week after treatment, the plants were observed and the results were recorded.

The following table reports the results of testing representative compounds of this invention in the broad spectrum test against foliar phytopathogens.

| Compound of Example No. | Late Blight | Bean Powdery Mildew | Anthracnose | Rice Blast | Helminthosporium |
|---|---|---|---|---|---|
| 1 | 1 | 1 | 1 | 3 | 1 |
| 2 | 1 | 1 | 1 | — | — |
| 6 | 3 | 1 | 1 | 1 | 1 |
| 7 | 1 | 1 | 1 | 1 | 1 |
| 8 | 1 | 1 | 1 | 1 | 1 |
| 9 | 1 | 1 | 1 | 1 | 1 |
| 10 | 1 | 1 | 1 | 1 | 1 |
| 13 | 1 | 1 | 4 | 1 | 1 |
| 14 | 1 | 1 | 1 | 1 | 1 |
| 15 | 1 | 1 | 1 | 3 | 1 |
| 16 | 1 | 1 | 1 | 1 | 1 |
| 17 | 1 | 1 | 1 | 1 | 1 |

In another informative test, the compound of Example 1, formulated as a 120 g./liter emulsifiable concentrate, was tested against powdery mildew of zinnia in field plots. The compound was applied six times at concentrations of 600 and 1200 ppm. on a 7-10 day spray schedule. By the end of the summer, the control plots were over 60 percent infected with powdery mildew. Under heavy disease pressure, the 600 ppm. treatment gave 70 percent disease control, and the 1200 ppm. treatment gave 95 percent control.

This invention is a method of reducing the adverse effects of foliar phytopathogens which comprises contacting the phytopathogens on the foliage with an effective amount of one of the compounds described above. The preferred compounds, with which the method is most advantageously carried out, are 4'-trifluoromethyl-2,4,6-trinitrodiphenylamine, 3'-trifluoromethyl-2,4,6-trinitrodiphenylamine, 4'-cyano-2,4,6-trinitrodiphenylamine, 2,3',4,6-tetranitrodiphenylamine, and 2,4,4',6-tetranitrodiphenylamine.

The preferred use of the method is in reducing the adverse effects of phytopathogens on the foliage of grapes. The most highly preferred use of the method is in reducing the adverse effects of *Plasmopara viticola*, the causative organism of grape downy mildew.

The method is carried out by applying one of the compounds described above to foliage where the compound comes into contact with the phytopathogens. Those skilled in plant protection will understand that use of the method does not necessarily kill the organisms. Depending on the application rate, the species and vigor of the phytopathogen, and the individual compound chosen, a greater or lesser proportion of the phytopathogen population will be killed and injured. It is well known that reducing the adverse effects of a phytopathogen, even though the disease is not completely eliminated, is of significant benefit to the treated plant. The above data show that application of the method of this invention produces worthwhile reduction of the adverse effects of phytopathogens, as indicated by reduced signs and symptoms of disease.

It is most effective to apply the compound to the foliage before the appearance of signs of infection. Thus, agriculturalists can use the method for the prevention of disease by applying one of the compounds at times when climatic factors are favorable for the growth of phytopathogens. The crop can thereby be protected from the injury which inevitably results from a pathogenic infection. It is also effective, however, to apply the compounds to the foliage after signs or symptoms of infection appear, although, in general, higher application rates of the compounds are necessary after an infection is established. Application of one of the compounds should be started as soon as possible after the first signs of infection appear, for best results.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion.

Compound concentrations in the range of from about 25 to about 1500 parts of compound per million parts by weight of the dispersion are used in the practice of this invention. Of course, from time to time, higher or lower concentrations will be useful, depending on the severity of the infection and the characteristics of the specific compound in use. The named range, however, encloses the usual optimum concentrations of the compounds.

The dispersions in which the compounds are applied to foliage are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1000 ppm., and may contain even more active ingredient.

Dispersions of the compounds are applied to foliage in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

We claim:

1. A method of reducing the adverse effects of downy mildew phytopathogens which comprises contacting the phytopathogens on the foliage of plants with an effective phytopathogen-inhibiting amount of a compound of the formula

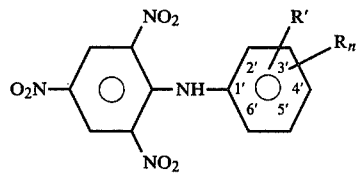

wherein R represents
   nitro,
   trifluoromethyl,
   hydroxy,
   cyano,
   benzoyl, or
   $C_1$-$C_3$ alkoxycarbonyl;
n represents 1-3;
R' represents
   hydrogen,
   chloro, or
   $C_1$-$C_3$ alkyl;
provided that benzoyl and $C_1$-$C_3$ alkoxycarbonyl do not occupy either the 2'- or 6'-position; that nitro does not occupy either the 2'- or 6'-position when n represents 1; that n must represent 1 when R represents cyano, benzoyl or $C_1$-$C_3$ alkoxycarbonyl; and that R' represents hydrogen when n represents 3.

2. A method of claim 1 wherein the amount of the compound is from about 25 to about 1500 ppm.

3. A method of claim 2 wherein the plants are grapes.

4. The method of claim 3 wherein the compound is 4'-trifluoromethyl-2,4,6-trinitrodiphenylamine.

5. The method of claim 2 wherein the compound is 3'-trifluoromethyl-2,4,6-trinitrodiphenylamine.

6. The method of claim 2 wherein the compound is 4'-cyano-2,4,6-trinitrodiphenylamine.

7. The method of claim 2 wherein the compound is 2,3',4,6-tetranitrodiphenylamine.

8. The method of claim 2 wherein the compound is 2,4,4',6-tetranitrodiphenylamine.

9. The method of claim 2 wherein the compound is 4'-trifluoromethyl-2,4,6-trinitrodiphenylamine.

* * * * *